US00PP32060P2

(12) United States Plant Patent
Fielding

(10) Patent No.: US PP32,060 P2
(45) Date of Patent: Aug. 11, 2020

(54) ***RANUNCULUS* PLANT NAMED 'ROCYELLOW'**

(50) Latin Name: ***Ranunculus cortusifolius* x *asiaticus***
Varietal Denomination: ROCYELLOW

(71) Applicant: John Fielding, London (GB)

(72) Inventor: John Fielding, London (GB)

( * ) Notice: Subject to any disclaimer, the term of this patent is extended or adjusted under 35 U.S.C. 154(b) by 0 days.

(21) Appl. No.: 16/501,915

(22) Filed: Jul. 2, 2019

(51) Int. Cl.
*A01H 5/02* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 5/02
See application file for complete search history.

(56) References Cited

PUBLICATIONS

GTITM UPOVROM Plant Variety Database Citation for 'ROCYELLOW' as per QZ PBR 20181386; Aug. 16, 2018; 1 page.*
PLUTO Plant Variety Database Citation for 'ROCYELLOW' as per QZ PBR 20181386; Aug. 16, 2018; 1 page.*

* cited by examiner

*Primary Examiner* — Kent L Bell
(74) *Attorney, Agent, or Firm* — Cassandra Bright

(57) ABSTRACT

A new and distinct *Ranunculus* cultivar named 'ROCYELLOW' is disclosed, characterized by cold-hardy plants producing multiple yellow flowers with red flecks The new variety is a *Ranunculus*, useful as an ornamental plant or for cut flower production.

2 Drawing Sheets

Figure 1:
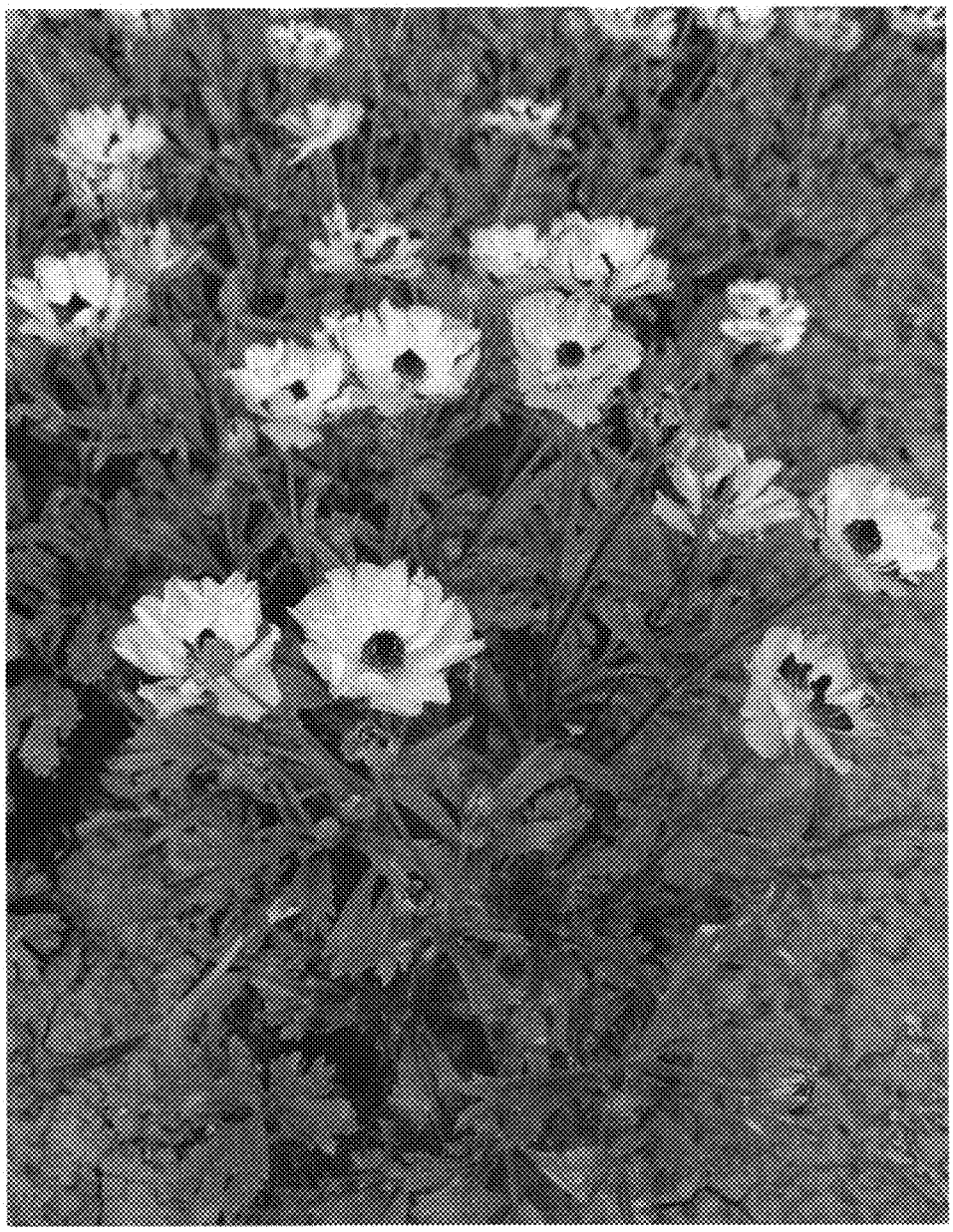

Latin name of the genus and species: *Ranunculus cortusifolius* x *asiaticus*.

Variety denomination: 'ROCYELLOW'.

BACKGROUND OF THE INVENTION

The new *Ranunculus* cultivar is a product of a planned breeding program conducted by the inventor, John Fielding in London, United Kingdom at his home garden. The objective was to produce varieties that are garden hardy in zone 8, and suitable for cut flower or garden uses. The cross resulting in this new variety was made in April of 2004.

The seed parent is an unnamed, unpatented *Ranunculus cortusifolius*. The pollen parent is an unnamed, unpatented *Ranunculus asiaticus*. The new variety was discovered in April 2009 by the inventor in a group of seedlings resulting from the 2004 crossing, in London, United Kingdom.

Asexual reproduction of the new cultivar was first performed by division in July 2009 at the inventor's home garden. The unique features of this cultivar are stable and reproduced true to type in more than 10 successive generations. Date of first sale of the new cultivar was Oct. 1, 2018, in the Netherlands.

SUMMARY OF THE INVENTION

The cultivar 'ROCYELLOW' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ROCYELLOW' These characteristics in combination distinguish 'ROCYELLOW' as a new and distinct *Ranunculus* cultivar:

1. Garden hardy in zone 7 or 8, has been observed to survive −15° Celsius in garden trials.
2. Can be used for cut flower or garden uses.
3. Cut flower will last in water for 12 to 14 days, with all flowers opening.
4. Branched stems with multiple flowers per stem.
5. Flower color is yellow with splashes and flecks of deep red.

PARENT COMPARISON

Plants of the new cultivar 'ROCYELLOW' are similar to plants of the seed parent, in most horticultural characteristics, however, plants of the new cultivar 'ROCYELLOW' differ in the following:

1. The seed parent is taller than the new variety.
2. Flowers of the new variety are yellow with red flecks, while the seed parent's flowers are golden yellow without markings.
3. The seed parent has 5 petals per flower, while the new variety has typically 17-21 petals.

Plants of the new cultivar 'ROCYELLOW' are similar to plants of the pollen parent, in most horticultural characteristics, however, plants of the new cultivar 'ROCYELLOW' differ in the following:

1. The pollen parent is shorter than the new variety.
2. The pollen parent is less winter hardy than the new variety.
3. The pollen parent has fewer flowers per stem than the new variety.

COMMERCIAL COMPARISON

Plants of the new cultivar 'ROCYELLOW' are comparable to the unpatented commercial variety *Ranunculus*

'Amandine Yellow Picotee'. The two *Ranunculus* varieties are similar in most horticultural characteristics; however, the new variety 'ROCYELLOW' differs in the following:

1. Vegetative carriage, foliage occurs lower on plants of the new variety.
2. Flowers of the new variety produce less petals and have an open center not found in this comparator.
3. The new variety is tolerant of more cold temperatures than this comparator.

BRIEF DESCRIPTION OF THE PHOTOGRAPHS

The accompanying photograph in FIG. 1 illustrates in full color flowering plants of the new variety at approximately 1 year old, grown outdoors.

Figure 2:
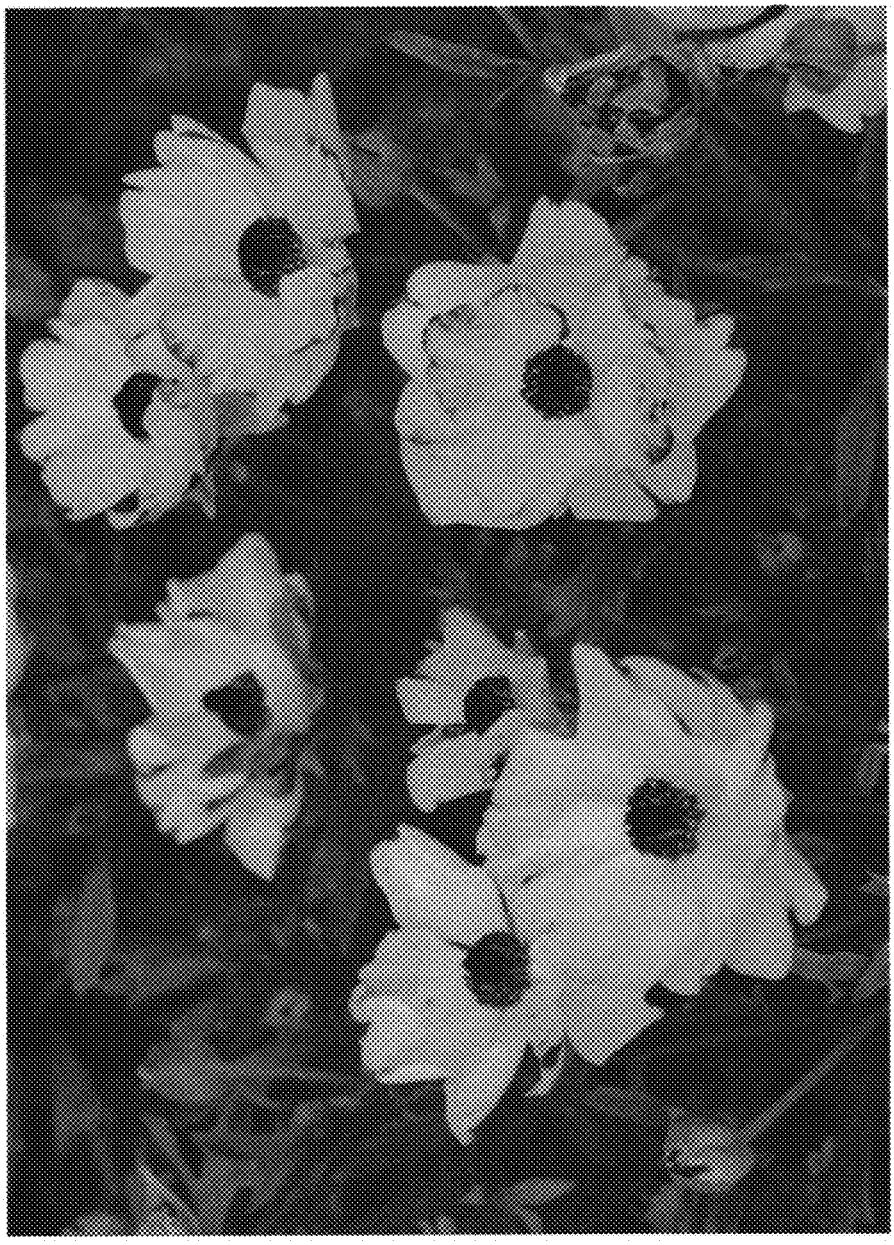

FIG. 2 illustrates a close-up view of flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 18-month-old 'ROCYELLOW' plants grown in a vented, unheated polytunnel in London, United Kingdom. No chemical treatments were performed. The growing temperature ranged from 5° C. to 25° C. during the day and from −5° C. to 10° C. during the night. General light conditions are bright, normal sunlight. Measurements and numerical values represent averages of typical plant types. Botanical classification: *Ranunculus cortusifolius* x *asiaticus* 'ROCYELLOW'.

PROPAGATION

Time to rooting: 15 days at approximately 10-15° C.
Time to produce a rooted plantlet: 20 days.
Root description: Secondary roots grow from the tuber and are fasciculate.

PLANT

Growth habit: Herbaceous perennial, robust, semi-erect.
Height to top flower: Average 54 to 65 cm.
Plant spread: Average 40 to 45 cm.
Growth rate: Medium to strong.
Branching characteristics: Branched panicle.
Length of lateral branches: Average range 12 to 29 cm.
Diameter of lateral branches: Average range 0.5 to 0.7 cm.
Texture of lateral branches: Glossy, slightly tomentose.
Internode length: Very close, forming basal rosette.
Strength of lateral branches: Medium to strong.
Color of lateral branches: Near RHS Yellow-Green 146B.
Aspect/angle of branches: 30° from vertical.
Number of leaves per lateral branch: Usually 2.

FOLIAGE

Basal leaf:

*Arrangement.*—Young Leaf: Trifoliate. Mature Leaf: Biternate.
*Average length.*—22 cm.
*Average width.*—10 cm.
*Overall shape of blade.*—Young Leaf: Obovate. Mature Leaf: Palmatifid to palmatipartite.
*Dissected leaves, describe lobes, quantity of dissection.*—Leaves generally lobed, in 3 parts, each further divided in 3 or more lobes. Lobes become more pronounced as leaf ages.
*Apex.*—Young leaf: Rounded. Mature leaf: Acute.
*Base.*—Rounded.
*Attachment.*—Base of the plant.
*Margin.*—Dentate.
*Texture of top surface.*—Glabrous to slightly tomentose.
*Texture of bottom surface.*—Glabrous.
*Appearance of top surface.*—Slightly glossy.
*Appearance bottom surface.*—Slightly glossy.
*Leaf internode length.*—Very close to form a basal rosette.
*Color.*—Young foliage upper side: RHS Yellow-Green 144A. Young foliage under side: RHS Yellow-Green 144A. Mature foliage upper side: Darker than RHS Yellow-Green 144A. Mature foliage under side: RHS Yellow-Green 144A.
*Venation.*—Type: Dichotomous; plunging into the limb at the upper surface; raised on the limb at the lower surface. Venation color upper side: RHS Yellow-Green 144B. Venation color under side: RHS Yellow-Green 144B.
*Petiole.*—Appearance: Long, tubular, rigid. Length: Average range 7 to 11 cm. Diameter: Average range 0.2 to 0.3 cm. Pubescence: Slightly tomentose. Color: RHS Yellow-Green 146B.

Leaf at the nodes of the stems:

*Arrangement.*—Biternate.
*Average length.*—11 to 13 cm.
*Average width.*—9 to 14 cm.
*Overall shape of blade.*—Palmatipartite.
*Dissected leaves, describe lobes, quantity of dissection.*—Generally divided in 3 parts, each one of which is further divided in many deeply incised lobes.
*Apex.*—Acute.
*Base.*—Acute.
*Attachment.*—Petiolate.
*Margin.*—Entire to serrate.
*Texture of top surface.*—Glabrous to slightly tomentose.
*Texture of bottom surface.*—Glabrous.
*Appearance of top surface.*—Slightly glossy.
*Appearance bottom surface.*—Slightly glossy.
*Leaf internode length.*—Average 6 to 13 cm.
*Color.*—Foliage upper side: RHS Yellow-Green 144B. Foliage under side: RHS Yellow-Green 144B.
*Venation.*—Type: Dichotomous, plunging into the limb at the upper surface and raised on the limb at the lower surface. Venation color upper side: RHS Yellow-Green N144A. Venation color under side: RHS Yellow-Green RHS N144B.
*Petiole.*—Appearance: Long, slightly flat, rigid. Length: Average 3 to 5 cm. Diameter: Average 0.4 to 0.8 cm. Pubescence: Slightly tomentose. Color: RHS Yellow-Green 146D.

FLOWER

Bloom period: Spring.
Vase life (cut flower): 12 to 14 days in water.
Rate of flower opening: 3 to 5 days from bud to open flower.
Flower longevity on plant: 5 to 7 days.
Persistent or self-cleaning: Self-Cleaning.
Bud:
*Closed bud.*—Shape: Ovate. Length: 0.8 to 1 cm. Diameter: 1 to 1.2 cm. Color: RHS Yellow-Green 144A.
*Slightly open bud.*—Shape: Flattened globular. Length: 1 to 1.2 cm. Diameter: 1.2 to 1.4 cm. Color: RHS Yellow-Green 144B; 144C at edge of sepals.
Flower size:
*Diameter.*—6 cm.
*Height.*—2.5 cm.
Corolla: Round, regular.
Petals:
*Arrangement.*—Semi-double, imbricated, disposed on the receptacle in very tight verticils. Size of petals variable, according to position, decreasing from exterior towards the center.
*Lobe length.*—2.8 cm.
*Lobe width.*—2.4 cm.
*Quantity.*—17-21.
*Texture.*—Silky, thin, glossy.
*Lobe apex.*—Rounded to retuse.
*Lobe shape.*—Obovate.
*Margin.*—Entire.
*Aspect.*—Concave with moderately incurved apex when fully open.
*Color when opening.*—Upper surface: RHS Yellow 6B. Flecks and splashes of Orange-Red N34A. Lower surface: Between RHS Yellow 7A and Greyed-Purple 185A. Flecks and splashes of Orange-Red N34A.
*Color fully opened.*—Upper surface: RHS Yellow 5A; fading to between 5C and 5D at apex. Flecks and splashes of Greyed-Purple 187B. Lower surface: Between RHS Yellow 3B and 4A; heavily splashed and flecked with Greyed-Purple 187B. Splashes and flecks cover approximately 15 to 40% of petal surface, with more splashes and flecks towards apex than near base.
Calyx/sepals:
*Quantity per flower.*—5.
*Shape.*—Concave.
*Length.*—1.5 to 1.7 cm.
*Width.*—0.6 to 0.8 cm.
*Apex.*—Acute.
*Base.*—Flat.
*Margin.*—Entire.
*Texture.*—Lower surface: Tomentose. Upper surface: Tomentose.
*Color.*—Outer Surface: RHS Yellow 2B; Yellow-Green 150C near base. Inner Surface: RHS Yellow-Green 150B, 144C at apex.
Peduncle: None.
Pedicel:
*Length.*—Average 12 to 23 cm.
*Diameter.*—Average 0.2 to 0.3 cm.
*Color.*—RHS Yellow-Green 146B.
*Orientation.*—Upright.
*Pubescence.*—Slightly tomentose.
Fragrance: None.

REPRODUCTIVE ORGANS

Androecium:
*Stamens.*—Numerous, short and completely surround the gynoecium.
*Anther shape.*—Slightly curved.
*Anther length.*—Approximately 0.7 cm.
*Anther color.*—RHS Greyed-Orange 187A; filament Yellow 7A.
*Pollen.*—Sparse.
Gynoecium: The pistils are numerous, short, locked together at the center of the corolla, dome-shaped apocarpous gynoecium.
*Height.*—Average 1.3 to 1.5 cm.
*Width.*—Average 0.5 to 0.6 cm.
*Shape.*—Domed, ovate.
*Pistil color.*—RHS Greyed-Purple N186C.

OTHER CHARACTERISTICS

Disease resistance: Typical for the species. Powdery mildew, leaf miner and rodent damage have all been observed in trials.
Drought tolerance and cold tolerance: More cold-hardy compared to other *Ranunculus* cultivars. Has survived −14° C. in trials in well-drained soil.
Fruit/seed production: Not observed.

What is claimed is:

1. A new and distinct cultivar of *Ranunculus* plant named 'ROCYELLOW' as herein illustrated and described.

* * * * *